US00PP29796P3

(12) United States Plant Patent
Beaumont

(10) Patent No.: US PP29,796 P3
(45) Date of Patent: Nov. 6, 2018

(54) ***TIBOUCHINA* PLANT NAMED 'BLAZE OF GLORY'**

(50) Latin Name: *Tibouchina organensis*
Varietal Denomination: Blaze of Glory

(71) Applicant: David Beaumont, Papakura (NZ)

(72) Inventor: David Beaumont, Papakura (NZ)

( * ) Notice: Subject to any disclaimer, the term of this patent is extended or adjusted under 35 U.S.C. 154(b) by 0 days.

(21) Appl. No.: 15/530,777

(22) Filed: Feb. 27, 2017

(65) Prior Publication Data

US 2018/0064009 P1 Mar. 1, 2018

(30) Foreign Application Priority Data

Aug. 31, 2016 (NZ) ..... PBR 33362

(51) Int. Cl.
*A01H 5/02* (2018.01)

(52) U.S. Cl.
USPC ..... Plt./226
CPC ..... *A01H 5/02* (2013.01)

(58) Field of Classification Search
None
See application file for complete search history.

*Primary Examiner* — Anne Marie Grunberg

(57) ABSTRACT

A new cultivar of *Tibouchina* plant named 'Blaze of Glory' that is characterized by green leaves with cream colored margins, a compact habit and purple flowers.

1 Drawing Sheet

Botanical classification: *Tibouchina organensis*.
Variety denomination: 'Blaze of Glory'.

BACKGROUND OF THE INVENTION

The present invention relates to a new and distinct cultivar of *Tibouchina* plant botanically known as *Tibouchina organensis* and hereinafter referred to by the cultivar name 'Blaze of Glory'.

'Blaze of Glory' is a naturally occurring branch mutation of *Tibouchina* 'Carol Lyn' (not patented). The new *Tibouchina* plant was discovered and selected by the Inventor as a single plant within a population of plants of 'Carol Lyn' in a controlled environment in a cultivated area of Papakura, New Zealand in 2013.

Asexual reproduction by leaf cuttings of the new cultivar 'Blaze of Glory' was first performed in 2014 in Papakura, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Tibouchina* cultivar 'Blaze of Glory'. These traits in combination distinguish 'Blaze of Glory' as a new and distinct cultivar apart from all other existing varieties of *Tibouchina* known to the inventor.

1. *Tibouchina* 'Blaze of Glory' exhibits green leaves with cream colored margins.
2. *Tibouchina* 'Blaze of Glory' exhibits a compact habit.
3. *Tibouchina* 'Blaze of Glory' exhibits purple flowers.

*Tibouchina* 'Blaze of Glory' can be compared to *Tibouchina* 'Moonstruck' (not patented) and plants of the species *Tibouchina urvilleana*. 'Blaze of Glory' is different than 'Moonstruck' in the following characteristics:

1. *Tibouchina* 'Blaze of Glory' exhibits green leaves with cream colored margins. In contrast, the leaves of 'Moonstruck' are entirely green.
2. *Tibouchina* 'Blaze of Glory' exhibits elliptic shaped leaves. In contrast, the leaves of 'Moonstruck' are ovate in shape.
3. *Tibouchina* 'Blaze of Glory' exhibits purple flowers. In contrast, the flowers of 'Moonstruck' are light pink.

'Blaze of Glory' is different than plants of the species *Tibouchina urvilleana* in the following characteristics:

1. *Tibouchina* 'Blaze of Glory' exhibits green leaves with cream colored margins. In contrast, the leaves of plants of the species *Tibouchina urvilleana* are green with pink and white colored margins.
2. *Tibouchina* 'Blaze of Glory' exhibits elliptic shaped leaves. In contrast, the leaves of plants of the species *Tibouchina urvilleana* are ovate in shape.

The closest comparison variety is the parent plant *Tibouchina* 'Carol Lyn'. 'Blaze of Glory' is different than 'Carol Lyn' in the following characteristics:

1. *Tibouchina* 'Blaze of Glory' exhibits green leaves with cream colored margins. In contrast, the leaves of 'Carol Lyn' are entirely green.
2. *Tibouchina* 'Blaze of Glory' exhibits a compact habit. In contrast, 'Carol Lyn' has a more open habit.
3. *Tibouchina* 'Blaze of Glory' exhibits smaller sized flowers that the flowers of 'Carol Lyn'.

BRIEF DESCRIPTION OF THE DRAWING

The accompanying photograph illustrates the distinguishing traits of *Tibouchina* 'Blaze of Glory'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Tibouchina* cultivar named 'Blaze of Glory'. Data was collected in Papakura, New Zealand from 12 month old greenhouse grown plants in 20 cm. diameter containers. The time of year was June and the temperature averaged 17° Centigrade during the day and 10° Centigrade at night. The light level was natural outdoor light. Color determinations are in accordance with The Royal Horticultural Society Colour Chart 2015 edition, except where general color terms of ordinary dictionary significance are used. The growing requirements are similar to the species.

'Blaze of Glory' has not been tested under all possible conditions and phenotypic differences may be observed with variations in environmental, climatic, and cultural conditions, however, without any variance in genotype.

Botanical classification: *Tibouchina organensis* 'Blaze of Glory'.

Plant type: Perennial shrub.

Parentage: 'Blaze of Glory' was discovered as a naturally occurring branch mutation of *Tibouchina* 'Carol Lyn'.

Vigor: Moderate.

Growth habit: Upright.

Plant shape: Globose.

Suitable container size: 20 cm. container.

Overall plant height: 35 to 40 cm.

Overall plant width: 35 to 40 cm.

Hardiness: USDA Zone 9.

Propagation: Terminal and leaf cuttings.

Time to initiate roots: Approximately 24 days to produce roots on an initial cutting at 20 degrees Centigrade.

Time to produce a rooted cutting or liner: Approximately 42 days at 20 degrees Centigrade.

Crop time: From a rooted cutting, approximately 32 weeks are required to produce a finished plant.

Root system: Fine and fibrous.

Stem:

*Branching habit.*—Basal branching.
*Average number of lateral branches.*—4.
*Pinching.*—Yes.
*Lateral branch diameter.*—Average 3.75 mm. in diameter.
*Lateral branch length.*—Average 30 cm. in length.
*Lateral branch strength.*—Moderate, pliable.
*Pubescence.*—Absent.
*Internode length.*—Average 3.8 cm. between nodes.
*Shape.*—Square in cross-section.
*Lateral branch angle.*—45 degrees from vertical.
*Texture.*—Smooth.
*Young stem color.*—199B.
*Mature stem color.*—199A.

Foliage:

*Leaf arrangement.*—Opposite.
*Compound or single.*—Single.
*Quantity of leaves per lateral branch.*—Average 12.
*Leaf shape.*—Elliptic.
*Leaf apex.*—Apiculate.
*Leaf base.*—Attenuate.
*Leaf length.*—Average 6.5 cm. in length.
*Leaf width.*—2.2 cm. in width.
*Texture.*—Leathery.
*Pubescence.*—Absent.
*Leaf margin.*—Entire.
*Vein pattern.*—Three main veins parallel to leaf axis, secondary veins horizontal to leaf axis.
*Young leaf color* (*lower surface*).—191B, margins 11C.
*Young leaf color* (*upper surface*).—NN137D, margins 11B.
*Mature leaf color* (*lower surface*).—191B, margins 11C.
*Mature leaf color* (*upper surface*).—NN137D, margins 11B.
*Vein color* (*lower surface*).—191B.
*Vein color* (*upper surface*).—NN137C.
*Leaf attachment.*—Petiolate.
*Petiole dimensions.*—Average 1.1 cm. in length and 1.6 mm. in width.
*Petiole color.*—58A.

Inflorescence:

*Inflorescence type.*—Compound cyme.
*Inflorescence aspect.*—Upward and outward.
*Inflorescence dimensions.*—Average 8.0 cm. in width and 8.0 cm. in height.
*Quantity of flowers per lateral stem.*—2 to 3.
*Quantity of flower buds per lateral stem.*—4 to 5.
*Flowering season.*—Winter in the Southern Hemisphere.
*Fragrance.*—Absent.
*Flower form.*—Actinomorphic.
*Flower bud length.*—16.3 mm. in length.
*Flower bud diameter.*—8.3 mm. in diameter.
*Flower bud shape.*—Ellipsoid.
*Bud color.*—142D, flushed 58D.
*Flower aspect.*—Outward.
*Flower dimensions.*—Average 5.0 cm. in diameter and 1.7 cm. in height.
*Flower longevity.*—1.5 to 2 weeks.
*Petal number.*—5.
*Petal texture.*—Smooth.
*Petal fused or unfused.*—Unfused.
*Petal shape.*—Broad Ovate.
*Petal margin.*—Entire.
*Petal apex.*—Rounded.
*Petal base.*—Attenuate.
*Petal dimensions.*—Average 2.95 cm. in length and 2.2 cm. in width.
*Petal color when opening* (*upper side*).—77A.
*Petal color when opening* (*under side*).—N78A.
*Petal color fully open* (*upper side*).—77A.
*Petal color fully open* (*under side*).—N78A.
*Petal color fading to.*—Not fading.
*Self-cleaning or persistent.*—Self-cleaning.

Sepals:

*Sepal arrangement.*—5 sepals in a whorl subtended from a sepaline cup, alternate with petals.
*Number of sepals.*—5.
*Sepal shape.*—Lanceolate.
*Sepal margin.*—Entire.
*Sepal apex.*—Acute.
*Sepal base.*—Fused into a cup.
*Sepal dimensions.*—5.2 mm. in length and 1.4 mm. in width.
*Sepal color* (*both sides*).—58D.
*Sepal strength.*—Strong.

Calyx:

*Calyx shape.*—Sepaline cup.
*Calyx dimensions.*—12.4 mm. in length and 19.3 mm. in diameter.

Peduncle:

*Peduncle dimensions.*—22.6 mm. in length and 2.34 mm. in diameter.
*Peduncle angle.*—45° from vertical.
*Peduncle color.*—NN137D with touches of 58A.
*Peduncle strength.*—Strong.

Pedicels:

*Pedicel dimensions.*—16.5 mm. in length and 1.25 mm. in diameter.

*Pedicel angle.*—45° from vertical.

*Pedicel color.*—NN137D.

*Pedicel strength.*—Strong.

Reproduction organs:

*Stamen number.*—10.

*Anther shape.*—Sickle shaped, geniculate.

*Anther dimensions.*—12 mm. in length.

*Anther color.*—78C.

*Amount of pollen.*—None observed.

*Pistil number.*—One.

*Pistil length.*—Average 32.1 mm.

*Stigma shape.*—Curved.

*Stigma color.*—144D.

*Style length.*—Average 22.7 mm.

*Style color.*—67B.

*Ovary color.*—67B.

Fruit and seed: 'Blaze of Glory' has not produced fruit or seed to date.

Disease and pest resistance: Disease and pest resistance has not been observed to date.

The invention claimed is:

1. A new and distinct variety of *Tibouchina* plant named 'Blaze of Glory' as described and illustrated.

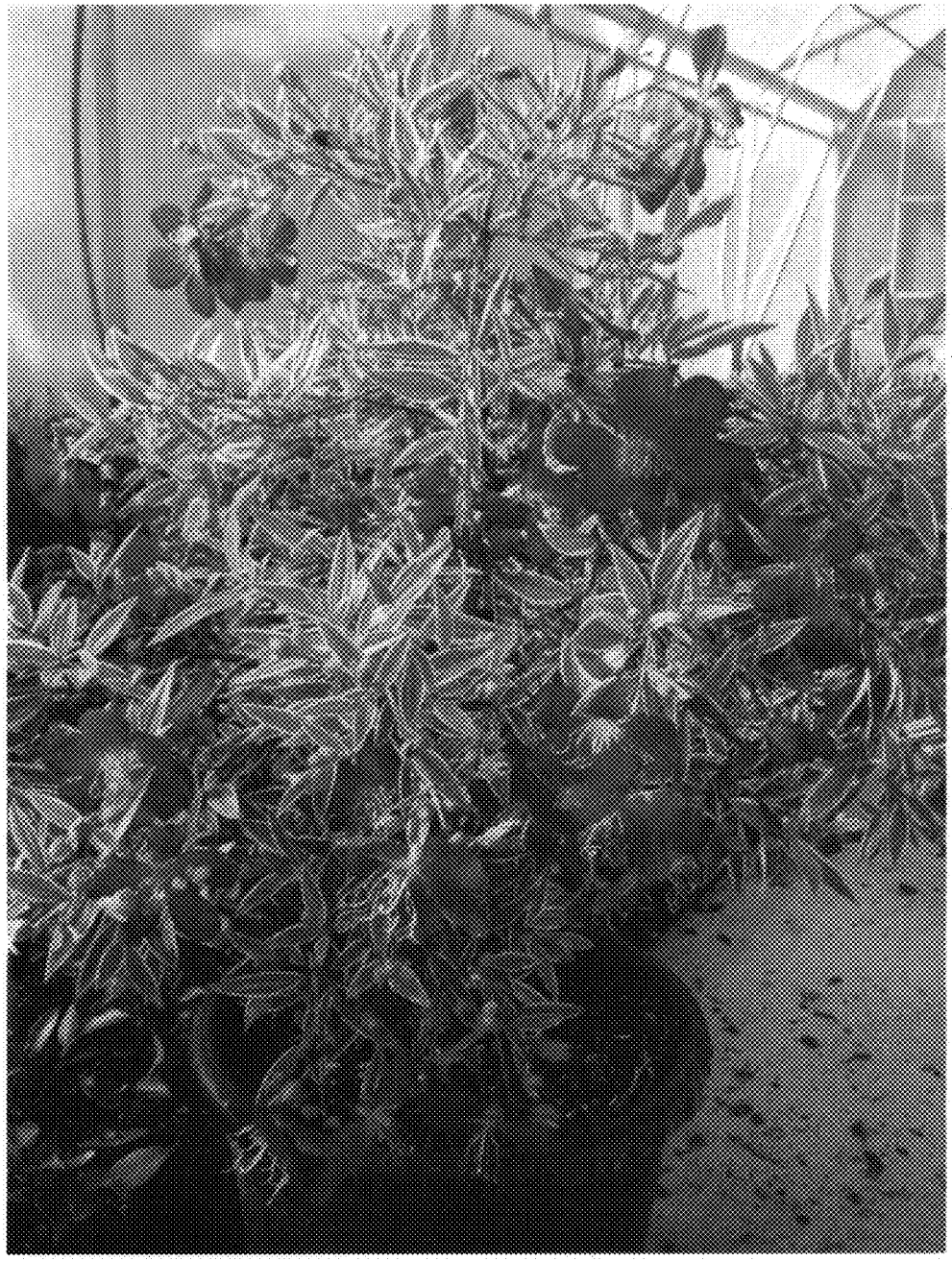

* * * * *